United States Patent [19]

Sugiura et al.

[11] Patent Number: 5,972,330
[45] Date of Patent: Oct. 26, 1999

[54] POISON BAITS CONTAINING N-PHENYL OR N-PYRIDYL PYRAZOLES FOR CONTROLLING INSECT PESTS

[75] Inventors: Masaaki Sugiura; Takashi Sugiyama, both of Hiroshima-ken, Japan

[73] Assignee: Rhone-Poulenc Agro, France

[21] Appl. No.: 09/043,905

[22] PCT Filed: Sep. 27, 1996

[86] PCT No.: PCT/FR96/01519

§ 371 Date: Aug. 24, 1998

§ 102(e) Date: Aug. 24, 1998

[87] PCT Pub. No.: WO97/11602

PCT Pub. Date: Apr. 3, 1997

[30] Foreign Application Priority Data

Sep. 27, 1995 [JP] Japan ................................ 7-249444

[51] Int. Cl.[6] ............................ A01N 25/00; C07D 31/44
[52] U.S. Cl. .................... 424/84; 546/275.4; 546/276.1; 548/367.4; 548/370.7; 548/371.7
[58] Field of Search ............................. 424/84; 548/367.4, 548/378.7, 371.7; 546/276.1, 275.4; 514/341, 407

[56] References Cited

U.S. PATENT DOCUMENTS

| | | | |
|---|---|---|---|
| 5,236,938 | 8/1993 | Huang et al. | 514/341 |
| 5,360,910 | 11/1994 | Huang et al. | 546/279 |
| 5,547,974 | 8/1996 | Hatton et al. | 514/406 |
| 5,567,429 | 10/1996 | Senbo | 424/405 |
| 5,614,182 | 3/1997 | Davidson et al. | 424/84 |

Primary Examiner—John Kight
Assistant Examiner—Charanjit S. Aulakh
Attorney, Agent, or Firm—Connolly, Bove, Lodge & Hutz, LLP

[57] ABSTRACT

A bait for controlling parasite pests, particularly insects, including a hydrated gelling agent and an active material such as a 1-arylpyrazole derivative.

20 Claims, No Drawings

POISON BAITS CONTAINING N-PHENYL OR N-PYRIDYL PYRAZOLES FOR CONTROLLING INSECT PESTS

This application is a 371 of PCT/FR96/01519 which is now published as WO/97/11602 on Mar. 4, 1997.

The invention relates to poisoned baits for controlling harmful insects.

The invention hopes to make available to users poisoned baits for combating harmful insects, which have excellent attractant and baiting properties and are highly effective against various insects which it is desired to control by using poisoned baits.

The invention relates to poisoned baits which can be used for controlling harmful parasites, in particular insects, and which are composed of an agent that gels upon hydration and comprise, as active material, a 1-arylpyrazole derivative of general formula (I):

in which:

$R_1$ represents a CN or methyl radical or a halogen atom;

$R_2$ represents $S(O)_nR_3$ or a 4,5-dicyanoimidazol-2-yl or haloalkyl radical $R_3$ represents an alkyl or haloalkyl radical;

$R_4$ represents hydrogen, a halogen atom or a radical selected from amongst the following radicals: $NR_5R_6$, $S(O)_mR_7$, $C(O)R_7$, $C(O)OR_7$, alkyl, haloalkyl, $OR_8$ and $N=C(R_9)(R_{10})$;

$R_5$ $R_6$ independently of one another represent a hydrogen atom or an alkyl, haloalkyl, C(O)alkyl, alkoxycarbonyl or $S(O)_rCF_3$ radical; or else $R_5$ and $R_6$ together can form a divalent alkylene radical which can be interrupted by one or more divalent hetero atoms such as oxygen or sulphur;

$R_7$ represents an alkyl or haloalkyl radical;

$R_8$ represents an alkyl or haloalkyl radical or a hydrogen atom;

$R_9$ represents an alkyl radical or a hydrogen atom;

$R_{10}$ represents a phenyl or heteroaryl radical which can optionally be unsubstituted or substituted by one or more halogen atoms or a radical selected from amongst the following radicals: —OH, —O-alkyl, —S-alkyl, cyano and alkyl;

$R_{11}$ and $R_{12}$ independently of one another represent hydrogen, a halogen atom or a CN or $NO_2$ radical, $R_{13}$ represents a halogen atom or a haloalkyl, haloalkoxy, $S(O)_qCF_3$ or $SF_5$ radical;

X represents a trivalent nitrogen atom or a C—$R_{12}$ radical, the three other valencies of the carbon atom forming part of the aromatic nucleus;

m, n and q independently of one another represent an integer equalling 0, one or two;

with the proviso that, if $R_1$ represents a methyl radical, then either $R_3$ represents a haloalkyl radical, $R_4$ represents $NH_2$, $R_{11}$ represents Cl, $R_{13}$ represents $CF_3$ and X represents N; or $R_2$ represents a 4,5-dicyanoimidazoly 2-Yl radical, $R_4$ represents Cl, $R_{11}$ represents Cl, $R_{13}$ represents $CF_3$ and X represents =C—Cl.

The alkyl radicals generally contain from 1 to 6 carbon atoms.

A preferred group of the 1-arylpyrazoles according to the invention is that in which:

$R_1$ represents CN; $R_3$ represents a haloalkyl radical; $R_4$ represents $NH_2$; X represents C—$R_{12}$;

$R_{11}$ and $R_{12}$ independently of one another represent a halogen atom; and $R_{13}$ represents a haloalkyl radical.

A particularly preferred compound is 5-amino-1-(2,6-dichloro-4-(trifluoromethylphenyl)-4-trifluoromethylsulphinyl-3-cyanopyrazole, which is termed "compound (A)" in the description hereinbelow. Compound (A) can be prepared by the processes described in European Patent Application A-0295117.

The compounds of general formula (I) can be prepared by known processes, for example those described in International Patent Applications Nos. WO 87/3781, 93/6089 and 94/21606 as well as in European Patent Applications 295117, 403300, 385809 or 679650, German Patent Application 19511269 and U.S. Pat. Nos. 5,232,940 and 5,236,938 or by other processes known to those in the art which are skilled in chemical synthesis, in particular through the publications in Chemical Abstract and in the literature to which these works refer. The compositions comprising the compounds of general formula (I) can also be prepared by prior-art methods or by similar methods.

The following products may be used, for example, as gelling agent according to the invention: Gellan gum, carrageenan gum, agar agar, gelatin, carob gum, xanthan gum, jelutong gum, polysaccharide gums. These gelling agents can be used alone or as a mixture of two or more in any ratio. Gellan gum is the preferred gum. Gellan gum is a natural polysaccharide which is isolated from cultures of Pseudomonas Elodea and contains glucose, glucoronic acid and rhamnose. It is also commercially available under the registered trade name Kelcogel by Kelco Company. The patents which relate to Gellan gum were published in Japanese Patent Applications S55-79397, filed on Jun. 14, 1980 (preparation), S59-88051, filed on May 21, 1984 (food compositions) and S60-11501, filed on Jan. 21, 1985 (unheated gel gum).

This invention also relates to a process for the preparation of poisoned baits which comprises making a liquid composition comprising gelling agent, water and a compound of general formula (I) and then solidifying the liquid composition to produce a gel. The hydrated gelling agent can be prepared, for example, by mixing a gelling agent and water, liquefying the mixture by heating it to a temperature of normally between 40 and 90° C. and solidifying it by cooling.

The poisoned baits which can be used according to the invention for controlling harmful parasites, for example insects, can be prepared, for example, by mixing the gelling agent and water, liquefying the mixture by heating, and adding the compound of general formula (I) as well as, for example, an attractant, a baiting substance, or, if required, other adjuvants, and solidifying the mixture by cooling. The products thus obtained can be formulated in any desired form by placing them into a suitable mould during the cooling and solidification process. Moreover, they can shaped as desired after solidification by processes including cutting, grinding and the like.

The weight ratio between gelling agent and water is generally between 0.001:99.999 and 50:50.

Unless otherwise stated, percentages in the present description are by weight.

The poisoned baits according to the present invention for combating harmful parasites, for example insects, generally comprise an attractant and a baiting substance. The following may be mentioned by way of example as baiting substance: cereal powders such as wheat powder, maize powder, rice powder, rice bran and the like, starches such as potato starch, maize starch and the like, sugars such as maltose, arabinose, galactose, lactose, sorbitose, glucose, molasses, honey and the like, and glycerol and the like. Attractants which may be mentioned by way of example are fatty acids such as caprylic acid, caproic acid, capric acid, lauric acid, oleic acid and the like, higher alcohols such as octyl alcohol, dodecyl alcohol, oleyl alcohol and the like, and flavours such as onion flavour, milk flavour, butter flavour and the like.

The poisoned baits according to the present invention for combating harmful insects may comprise, as other adjuvants, a stabilizer, a repellent for those species which one does not want to ingest the baits, a colorant, an antiseptic and the like. Stabilizers which may be mentioned are, for example, a calcium salt such as calcium lactate, calcium chloride and the like. Repellents which may be mentioned are, for example, hot or bitter substances such as Guinea pepper powder, dinatonium benzoate and the like. Colorants which may be mentioned are, for example, Red No. 2, Red No. 102, Yellow No. 4, Yellow No. 5, caramel and the like. Antiseptics which may be mentioned are, for example, sorbic acid, sorbinates, paraoxybenzoic esters and the like.

The poisoned baits according to the present invention for combating harmful parasites, for example insects, generally comprise between $1 \times 10^{-5}$ and 50% of compound of general formula (I), generally between $1 \times 10^{-3}$ and 99.99% of gelling agent, generally between $1 \times 10^{-3}$ and 99.99% of attractants and baiting agents, and between 0 and 99.99% of other adjuvants.

Moreover, the poisoned baits for combating harmful parasites, for example insects, can comprise other insecticidally active materials in addition to the compound of the general formula (I).

The poisoned baits according to the present invention for combating harmful parasites, for example insects, can be used for controlling various insects by placing them in locations where the harmful insects live, or through which they pass, either in the form of poisoned baits alone or by placing them into suitable containers.

Amongst the harmful parasites which can be destroyed there may be mentioned not only insects such as cockroaches, in particular the German cockroach (*Blatella germanica*), the smoky-brown cockroach (*Periplaneta fuliginosa*), flies such as the housefly, ants such as *Formica fusca japonica, Tetramorium cacspitum, Lasius niger, Monomorium pharanois, Crematogaster laboriosa, Pristomyrmex pungens, Monomorium nipponense, Pheidole nodus, Brachyponcra chinensis, Camponotus japonicus, Iridomyrmex itoi,* the fire ant, the Carpenter ant, but also other arthropods, in particular crustaceans such as various armidillidia, in particular *Armidillidium vulgare* and the like. Even though the rates of application of the poisoned baits which can be used for combating harmful parasites, for example insects, can vary depending on the target species, the conditions under which they appear and the like, it is still possible to say that the doses of compound of formula (I) to be used are, for example, between $1 \times 10^{-4}$ and 500 mg per 100 m$^2$ in the case of domestic applications, for example for combating cockroaches, and in the case of applications outside for example against ants or Armadillidia. The doses of compound of formula (I) in the baits are generally between $1 \times 10^{-4}$ and 500 mg per bait.

The present invention can be illustrated in greater detail by a few use examples.

The examples which follow are preparation examples of formulations which can be used in accordance with the invention.

PREPARATION EXAMPLE 1

1 g of Gellan gum and 68.7 g of water were mixed and then heated with stirring to 80–90° C. to give a homogeneous solution; 0.1 g of compound (A) and 0.2 g of calcium lactate were then added with stirring, followed by 30 g of honey, still with stirring; the mixture obtained was poured into a cylinder of 3.0 cm diameter, cooled and solidified to give poisoned baits.

PREPARATION EXAMPLE 2

The poisoned baits for combating harmful insects can be prepared by the same method as described in Preparation Example 1, except that 0.01 g of compound (A) is used instead of 0.1 g.

PREPARATION EXAMPLE 3

The poisoned baits for combating harmful insects can be prepared by the same method as described in Preparation Example 1, except that 0.001 g of compound (A) is used instead of 0.1 g.

The examples which follow are experimental examples.

EXPERIMENTAL EXAMPLE NO. 1

A wooden cage, water, solid feed and poisoned baits were placed into an acrylic resin container (25 cm×25 cm×10 cm); then, 90 adult female German cockroaches were introduced.

The number of dead German cockroaches was counted at regular intervals. The results are shown in Table 1.

Moreover, and by way of comparison, the results obtained with poisoned baits (Comparison Example 1) prepared by mixing 0.1 g of compound (A), 30 g of honey, 20 g of mashed potato and 10 g of rice bran are also given in Table 1.

TABLE 1

| | Number of dead insects | | |
|---|---|---|---|
| Time (hours) | Preparation Example 1 | Preparation Example 2 | Comparison Example 1 |
| 6 | 62 | 44 | 20 |
| 9 | 83 | 80 | 51 |
| 12 | 88 | 84 | 68 |
| 24 | 90 | 89 | 80 |
| 27 | | 90 | 80 |
| 30 | | | 82 |
| 48 | | | 88 |
| 72 | | | 90 |

EXPERIMENTAL EXAMPLE NO. 2

A wooden cage, water, solid feed and poisoned baits were placed into an acrylic resin container (25 cm×25 cm×10 cm); then, 30 adult female smoky-brown cockroaches (*Periplaneta fuliginosa*) were introduced.

The number of dead smoky-brown cockroaches was counted at regular intervals. The results are shown in Table 2.

Moreover, and by way of comparison, the results obtained with poisoned baits (Comparison Example 1) prepared by mixing 0.1 g of compound (A), 30 g of honey, 20 g of mashed potato and 10 g of rice bran are also given in Table 2.

TABLE 2

| Time (hours) | Number of dead insects | | |
|---|---|---|---|
| | Preparation Example 1 | Preparation Example 2 | Comparison Example 1 |
| 9 | 22 | 1 | 0 |
| 12 | 24 | 7 | 1 |
| 24 | 28 | 26 | 15 |
| 30 | 30 | 27 | 15 |
| 48 | | 27 | 21 |
| 72 | | 30 | 25 |
| 96 | | | 27 |

EXPERIMENTAL EXAMPLE NO. 3

A wooden cage, water, solid feed and poisoned baits were placed into a plastic container (whose bottom measured 9 cm in diameter); then, 60 adult *Pristomyrmex pungens* were introduced.

The number of dead insects (*Pristomyrmex pungens*) was counted at regular intervals. The results are given in Table 3

TABLE 3

| Time (hours) | Number of dead insects | | |
|---|---|---|---|
| | Preparation Example 1 | Preparation Example 2 | Comparison Example 1 |
| 24 | 51 | 43 | 7 |
| 48 | 60 | 58 | 20 |
| 72 | | 60 | 52 |
| 96 | | | 60 |

EXPERIMENTAL EXAMPLE NO. 4

A certain amount of soil, a china box, water, cabbage leaves and poisoned baits were placed into an acrylic resin container (25 cm×25 cm×10 cm); then, 50 adult *Armadillidium vulgare* were introduced.

The number of dead insects (*Armadillidium vulgare*) was counted at regular intervals. The results are shown in Table 4.

TABLE 4

| Time (hours) | Number of dead insects | |
|---|---|---|
| | Preparation Example 1 | Preparation Example 2 |
| 1 | 21 | 24 |
| 2 | 40 | 39 |
| 3 | 46 | 45 |
| 4 | 49 | 46 |
| 5 | 50 | 48 |
| 6 | | 50 |

As is evident from reading the different results of the experiments, the poisoned baits according to the present invention for combating harmful insects have an outstanding efficacy for combating various harmful parasites, for example insects. Moreover, as can be seen from the results of the comparison examples, the poisoned baits according to the invention have a much better efficacy than the reference formulations which comprise the same amount of substance [compound of general formula (1)].

The poisoned baits according to the present invention for combating harmful parasites, for example insects, have an outstanding efficacy for combating various harmful parasites, for example insects.

We claim:

1. Antiparasitic bait comprising a hydrated agent and a active material, characterized in that it is composed of an agent which gels upon hydration, by way of basic substance, and comprising, by way of active material, a compound of general formula (I):

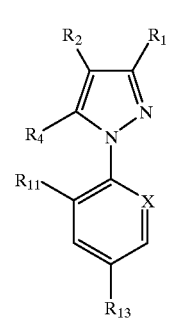

in which:

$R_1$ is CN or methyl or a halogen atom;

$R_2$ is $S(O)_n R_3$ or 4,5-dicyanoimidazol 2-yl or haloalkyl;

$R_3$ is alkyl or haloalkyl;

$R_4$ represents a hydrogen, halogen atom, $NR_5R_6$, $S(O)_m R_7$, $C(O)R_7$, $C(O)O—R_7$, alkyl, haloalkyl, $OR_8$ or $—N=C(R_9)R_{10}$;

$R_5$ and $R_6$ independently represent a hydrogen atom, alkyl, haloalkyl, C(O)alkyl, alkoxycarbonyl or $S(O)_r CF_3$ radical; or $R_5$ and $R_6$ can together form a divalent alkylene radical which can be interrupted by one or two divalent heteroatoms, $R_7$ represents an alkyl or haloalkyl radical;

$R_8$ represents an alkyl or haloalkyl radical or a hydrogen atom;

$R_9$ represents an alkyl radical or a hydrogen atom;

$R_{10}$ represents a phenyl or heteroaryl group which may optionally be unsubstituted or substituted by one or more halogen atoms or a member of the group consisting of —OH, —O-alkyl, —S-alkyl, cyano and alkyl;

$R_{11}$ and $R_{12}$ represent, independently of one another, a hydrogen, halogen atom, CN or $NO_2$;

$R_{13}$ represents a halogen atom, a haloalkyl, haloalkoxy, $S(O)_q CF3$ or $SF_5$ group;

X represents a trivalent nitrogen atom or a C—$R_{12}$ radical, the other three valences of the carbon atom forming part of the aromatic ring;

m, n, q and r represent, independently of one another, an integer equal to 0, 1 or 2; provided that, when $R_1$ is methyl, then either $R_3$ is haloalkyl, $R_4$ is $NH_2$, $R_{11}$ is Cl, $R_{13}$ is $CF_3$ and X is N; or then $R_2$ is 4,5-dicyanoimidazol 2-yl, $R_4$ is Cl, $R_{11}$ is Cl, $R_{13}$ is $CF_3$ and X is =C—Cl.

2. Bait according to claim 1, in which $R_1$ is CN;

$R_3$ is a haloalkyl radical;

$R_4$ is $NH_2$;

X is $C-R_{12}$;

$R_{11}$ and $R_{12}$ represent, independently of one another, a halogen atom and $R_{13}$ is a haloalkyl radical.

3. Bait according to claim 1, in which the compound of formula (I) is 5-amino 1-(2,6-dichloro 4-trifluoromethyl phenyl) 4-trifluoromethylsulfinyl 3-cyanopyrazole.

4. Bait according to claim 1, wherein said bait is an insectide and is effective against parasites.

5. Bait according to claim 1, in which the gelling agent is gellan gum, carrageenan, agar-agar, gelatine, locust bean gum, xanthan gum, jelutong gum or polysaccharide gum.

6. Bait according to claim 1, which has been shaped.

7. Bait according to claim 1, in which the ratio between gelling agent and water is between 0.001:99.999 and 50:50.

8. Bait according to claim 1, which comprises between $1 \times 10^{-5}$ and 50% of the compound of formula (I), between $1 \times 10^{-3}$ and 50% of gelling agent, from $1 \times 10^{-3}$ to 99.99% of attractant or baiting agent and between 0 to 99.99% of other adjuvants.

9. Process for the preparation of a poisoned bait according to claim 1, which comprises preparing a liquid composition comprising a gelling agent, water and compound of formula (I) and solidifying the liquid composition to form a gel.

10. Process for controlling parasites in a place with poisoned bait according to claim 1.

11. Process according to claim 10 in which compound of formula (I) is employed at doses between $1 \times 10^{-4}$ and 500 mg per 100 $m^2$.

12. Process according to claim 10 in which the poisoned bait comprises compound of formula (I) at doses between $1 \times 10^{-4}$ and 500 mg per bait.

13. The bait as claimed in claim 1, wherein $R_5$ and $R_6$ together form a divalent alkylene radical which can be interrupted by one or two oxygen or sulfur heteroatom.

14. The bait according to claim 1, wherein the bait is an insecticide bait and the compound of formula I is 5-amino 1-(2,6-dichloro 4-trifluoromethyl phenyl) 4-trifluoromethylsulfinyl 3-cyanopyrazole.

15. The bait according to claim 14, wherein the gelling agent is gellan gum, carrageenan, agar-agar, gelatine, locust bean gum, xanthan gum, jelutong gum or polysaccharide gum.

16. The bait according to claim 15, wherein the gellan gum.

17. The bait according to claim 1, wherein $R_2$ is 4,5-dicyanoimidazol 2-yl or haloalkyl.

18. The bait according to claim 1, wherein X is a trivalent nitrogen.

19. The bait according to claim 1, wherein $R_4$ represents a hydrogen, halogen atom, $NR_5R_6$, $S(O)_mR_7$, $C(O)R_7$, $C(O)O-R_7$, alkyl, haloalkyl or $OR_8$.

20. The bait according to claim 19, wherein $R_4$ represents a hydrogen, halogen atom, $S(O)_mR_7$, $C(O)R_7$, $C(O)O-R_7$, alkyl, haloalkyl or $OR_8$.

* * * * *